(12) United States Patent
Carballada et al.

(10) Patent No.: US 7,380,556 B2
(45) Date of Patent: Jun. 3, 2008

(54) HAIR IRON

(75) Inventors: Jose A. Carballada, Cincinnati, OH (US); Dennis E. Kuhlman, Middletown, OH (US); David M. Stentz, Cincinnati, OH (US); Shinji Nishimura, Hikone (JP); Kazunori Nakasai, Hikone (JP)

(73) Assignees: Matsushita Electric Works, Ltd., Osaka (JP); The Procter & Gamble Company, Cincinnati, OH (US)

( * ) Notice: Subject to any disclaimer, the term of this patent is extended or adjusted under 35 U.S.C. 154(b) by 334 days.

(21) Appl. No.: 10/516,110

(22) PCT Filed: Jun. 26, 2002

(86) PCT No.: PCT/JP02/06411

§ 371 (c)(1),
(2), (4) Date: Jul. 7, 2005

(87) PCT Pub. No.: WO2004/002262

PCT Pub. Date: Jan. 8, 2004

(65) Prior Publication Data

US 2006/0144414 A1 Jul. 6, 2006

(51) Int. Cl.
*A45D 1/00* (2006.01)
*A45D 2/40* (2006.01)
*A45D 6/06* (2006.01)
*A45D 1/04* (2006.01)

(52) U.S. Cl. .......... 132/224; 132/225; 132/228; 132/227; 132/226; 219/225

(58) Field of Classification Search ........ 132/224–229; 219/225–229; 251/337
See application file for complete search history.

(56) References Cited

U.S. PATENT DOCUMENTS 4,034,201 A 7/1977 Walter et al.

(Continued)

FOREIGN PATENT DOCUMENTS

JP 63-123203 U 8/1988

(Continued)

OTHER PUBLICATIONS

JPO Notification of Reasons for Refusal, App. #2004-517204, Dispatch #191131, Dispatch Date Apr. 24, 2007 (5 pages).

(Continued)

*Primary Examiner*—Robyn Doan
(74) *Attorney, Agent, or Firm*—Cheng Law Group PLLC

(57) ABSTRACT

A hair iron that can set hairstyles by heating and spraying a treatment agent comprises a pair of holding parts (1, 1); each having heating block (2), the surface of which acts as a holding surface (7); at least one holding part (1) containing liquid container (5), liquid holder (4) that brings the liquid in liquid container (5) in contact with heating block (2) as the liquid in liquid container (5) is transferred to heating block (2), and steam path (19) that sprays from holding surface (7) the steam generated as the liquid transferred from inside liquid container (5) is heated by the contact surface with heating block (2) of liquid holder (4). Hair is held between the holding surfaces (7, 7) of the pair of holding parts (1, 1), and under the action of the steam sprayed from the steam path (19), the hairstyle is set. In this hair iron (40), the liquid container (5) is set on the side of the heating block (2) opposite to the holding surface (7), and at the same time, the liquid holder (4) is set between the heating block (2) and the liquid container (5).

18 Claims, 11 Drawing Sheets

U.S. PATENT DOCUMENTS 5,567,428 A * 10/1996 Hughes .................. 424/401
6,056,946 A    5/2000 Crudele et al.
7,178,531 B2 *  2/2007 Carballada et al. ......... 132/224

FOREIGN PATENT DOCUMENTS

JP  08-080215 A1  3/1996
JP  2000-157322 A1  6/2000

OTHER PUBLICATIONS

International Search Report for PCT/JP02/06411 mailed on Mar. 14, 2003.

* cited by examiner (b)

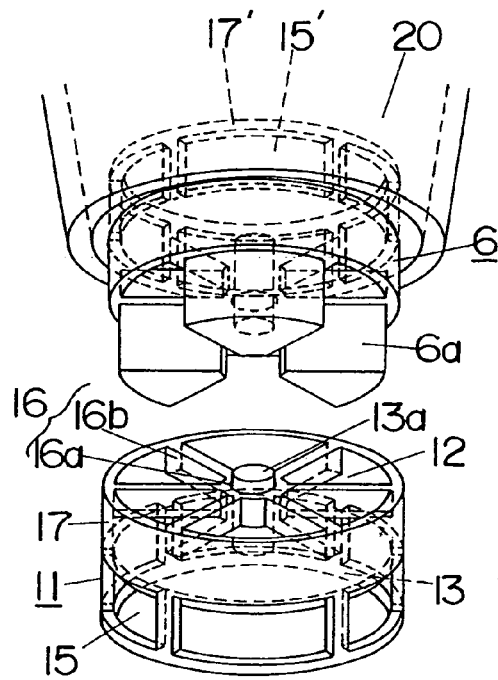
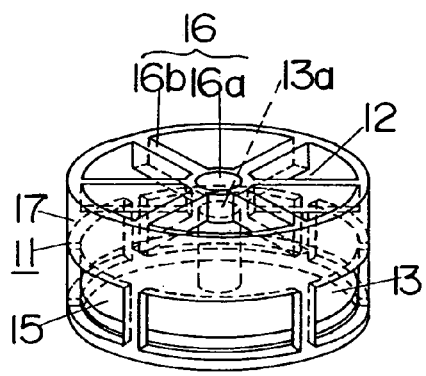
FIG. 6A  FIG. 6B
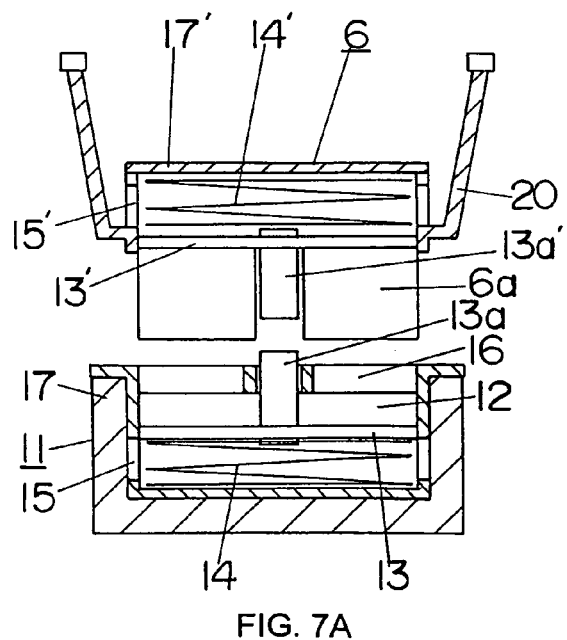
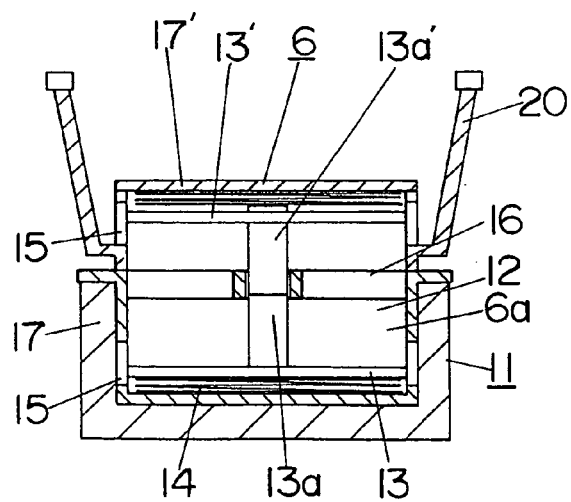
FIG. 7A  FIG. 7B

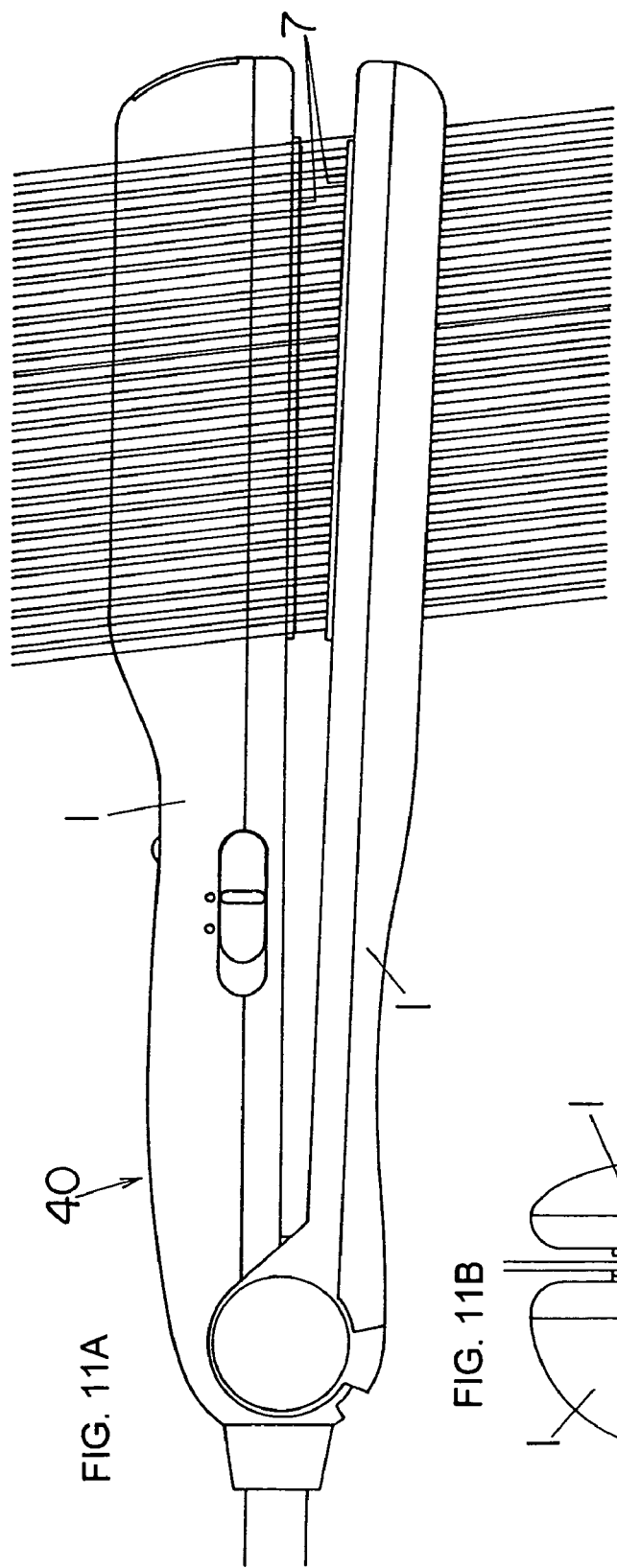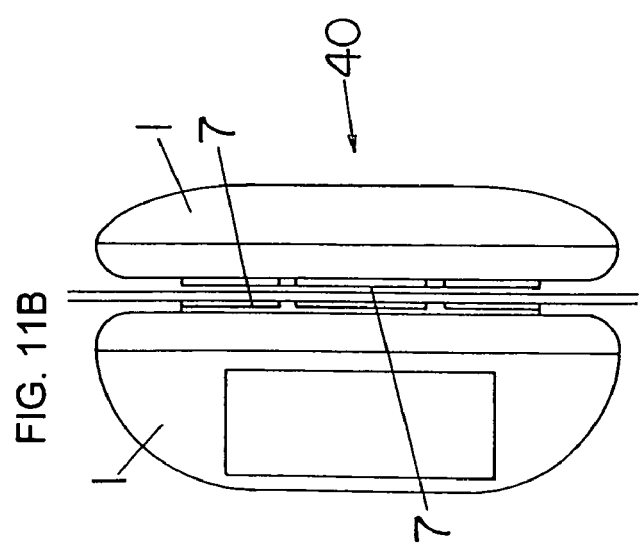

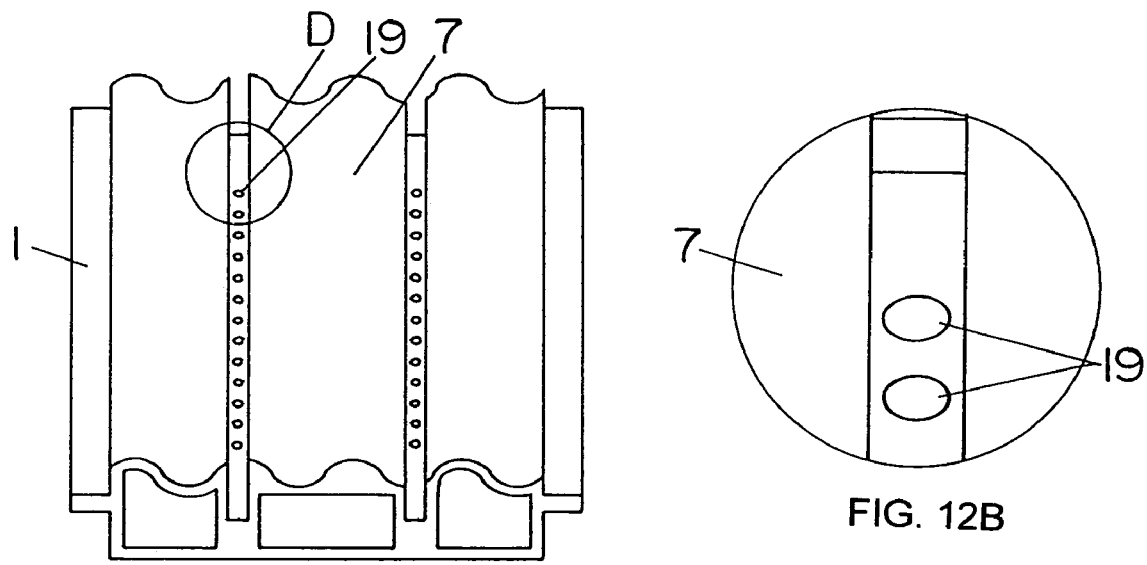
FIG. 12A
FIG. 12B
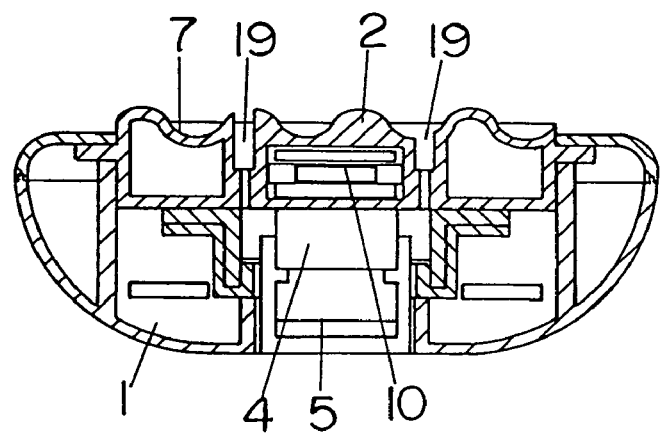
FIG. 13

HAIR IRON

TECHNICAL FIELD

The present invention relates to a type of hair iron that sets hairstyles by heating and spraying a treatment agent.

BACKGROUND ART

Hair irons usually comprise a pair of holding parts that are equipped with heating blocks and that are hinged at one end, where at least one of the holding parts has a steam spraying means. The hair is held between the opposing surfaces of the pair of holding parts so that it can be set to the desired hairstyle with heat and steam.

As described in Japanese Patent Early Publication [kokai] No. 2000-157322, etc., the conventional steam spraying means has a liquid container at the end of a holding part. One end of the liquid holder, such as a piece of felt, is in contact with the liquid in the liquid container, while the other end of the liquid holder is in contact with a heating block. In this constitution, the liquid that has been transferred by the liquid holder to the heating block evaporates, and steam is sprayed from the holding surface of the holding part.

In the aforementioned conventional hair iron, the liquid container is located closer to the end of the holding part than the heating block, and the other end of the liquid holder that has one end in contact with the liquid container is in contact with a heater inside the heating block that is held by the other end of the liquid holder. Consequently, in the liquid holder, the liquid in the portion farther from the liquid container is more difficult to transfer, and it is thus impossible to generate steam uniformly from the various portions of the liquid holder in contact with the heating block.

SUMMARY OF THE INVENTION

The purpose of the present invention is to solve the aforementioned problems of the conventional methods by providing a hair iron that can generate steam uniformly with great efficiency from the various portions of the liquid holder in contact with the heating block by transferring the liquid uniformly.

In order to solve the aforementioned problems, the present invention provides a type of hair iron characterized in that it comprises a pair of holding parts (1, 1); where each holding part has at least one heating block (2) which has a holding surface (7); at least one of the holding parts (1), in turn comprises liquid container (5), liquid holder (4) that brings the liquid in the liquid container (5) in contact with the heating block (2) as the liquid in the liquid container (5) is transferred to the heating block (2), and steam path (19) that sprays from the holding surface (7) the steam that is generated as the liquid transferred from inside the liquid container (5) is heated by the contact surface with the heating block (2) of the liquid holder (4); wherein hair is held between the holding surfaces (7, 7) of the pair of holding parts (1, 1), and under the action of the steam sprayed from the steam path (19), the hairstyle is set; and wherein in the hair iron (40), the liquid container (5) is arranged on the side of the heating block (2) opposite the holding surface (7), and, at the same time, the liquid holder (4) is arranged between the heating block (2) and the liquid container (5).

With this constitution, it is possible to have the liquid in the liquid container (5) transferred uniformly to the entire contact surface of the holding part (4) with the heating block (2), and it is possible to stably generate steam with great efficiency from the various portions of the liquid holder (4) in contact with the heating block (2).

In the present invention, it is preferred that with respect to each of the dimensions in various directions of the contact surface of the liquid holder (4) with the heating block (2), the dimension of the liquid container (5) in the same direction be formed nearly the same or larger. In this case, the liquid container is of sufficient volume to extend the continuous time of evaporation. Therefore, it is possible to extend the period of steam generation by use of the liquid container (5) with large capacity.

It is also preferred that part of the liquid holder (4) is located inside the liquid container (5). In this case, even when the orientation of holding part (1) itself is changed, it is still possible to generate steam continuously as the liquid in the liquid container (5) is brought in contact with the liquid holder (4).

In addition, it is preferred that the liquid container (5) and the liquid holder (4) are integrally formed. In this case, it is possible to ensure easy connection between the liquid container (5) and the liquid holder (4).

It is further preferred that the liquid container (5) and liquid holder (4) be arranged such that they allow quick-connecting-disconnecting as a single unit to/from the holding part (1). In this case, there is also the following effect: when the liquid is supplemented, one can remove both of the liquid container (5) and the liquid holder (4) as a single unit. As a result, it is possible to prevent contamination of the hair iron (40) with the liquid, or short-circuits of the electrical circuit or internal damage due to invasion of the liquid into the hair iron. Also, since the liquid holder (4) and the liquid container (5) are integrated, even when attachment/detachment is performed repeatedly; the connection between the liquid container (5) and the liquid holder (4) still can be easily ensured.

In addition, it is preferred that a supplementary liquid injection unit (11) be arranged in the liquid container (5), and, at the same time, a connecting means be arranged such that it can supply liquid from a liquid storage container (20) arranged as a separate part only when a liquid supply unit (6) of the liquid storage container (20) is fitted to the supplementary liquid injection unit (11). In this case, it is possible to prevent replenishment of the liquid from the wrong container or means, so that it is possible to avoid injection and use of unwanted liquid.

It is preferred that as the connecting means, the supplementary liquid injection unit (11) is equipped with a recession-shape connecting path (12) in which the liquid supply unit (6) of the liquid storage container (20) can be inserted and fitted, a sealing plate (13) that seals the connecting path (12), and a spring (14) that energizes the sealing plate (13) toward the opening of the connecting path (12); in the state in which the liquid supply unit (6) is not fitted, the connecting hole (15) that connects the interior of the connecting path (12) and the interior of the liquid container (5) is located on the side of the inner bottom surface of the connecting path (12) with respect to the sealing plate (13) that is energized and positioned by the spring toward the opening of the connecting path (12); and, in the state in which the liquid supply unit (6) is fitted, at least part of the connecting hole is located on the side of the opening of the connecting path (12) with respect to the sealing plate (13) that is pressed and positioned into the liquid supply unit (6). In this constitution, there is also the following effect: only the liquid from dedicated liquid storage container (20) equipped with the liquid supply unit (6) that is fitted to the supplementary liquid injection unit (11) can be injected into the liquid container (5). Consequently, with high reliability, it is possible to avoid injection and use of undesired liquid.

It is also preferred that the contact surface of the liquid holder (4) with the heating block (2) is formed in an elongated shape extending in the longitudinal direction of the holding surface (7), and, at the same time, a steam chamber (3) is formed on the side of the liquid holder (4); multiple steam paths (19) that pass from the steam chamber (3) to the holding surface (7) are formed at prescribed longitudinal intervals. In this constitution, it is possible to apply steam to the hair held between holding surfaces (7, 7) uniformly over the longitudinal direction of holding surface (7).

It is further preferred that steam chambers (3) be formed on both sides of the liquid holder (4), and that steam paths (19) be formed for connecting from the steam chambers (3) on the two sides. In this way, it is possible to apply steam uniformly over all the hair held between holding surfaces (7, 7).

In addition, it is preferred that the holding parts (1, 1) be elongated in form, with a holding surface (7) formed on one end and a handle (8) formed on the other end, and, at the same time, that the handle ends of the holding parts (1, 1) be connected together so that one of the holding parts can be pivotally move relative to the other one of the holding parts about the handle ends. As a result, the two holding parts can be opened/closed as desired. In this way, the hair can be easily held between the holding parts (1, 1) with only one hand, and the holding force can easily be adjusted.

Moreover, it is preferred that only one of the holding parts (1, 1) is a holding part (1) on the steam spraying side, which is equipped with the liquid container (5), the heating block (2), the liquid holder (4), and the steam path (19); the other holding part is holding part (1) on the heating side; and that there is a power source switch unit (33) for switching between a first power supply mode where electric power is supplied to the heating blocks (2, 2) of both holding parts (1, 1), and a second power supply mode where electric power is supplied only to the heating block (2) of the holding part (1) on the steam spraying side or the heating side. In this way, it is possible to turn on/off the steam spray and heating selectively, so that varied application methods can be realized.

It is also preferred that both of the pair of holding parts (1, 1) be equipped with the heating block (2), the liquid holder (4), the liquid container (5) and the steam path (19). In this way, it is possible to spray steam on both sides of the hair held between the holding surfaces (7, 7), so that the liquid can effectively penetrate into the hair.

In addition, it is preferred that the liquid injected into the liquid container be a treatment agent. The present invention provides a treatment agent to the hair in order to achieve a desired style. The treatment agent can provide a style achievement by providing conditioning/lubrication benefit to hair fibers and/or making it easier to reshape hair. All of this results in a hair that is more manageable and can more easily take the new desired shape. The treatment agent of the present invention may be any known or otherwise effective volatile liquid that ease hair manageability and will evaporate from hair, while or after shape has been achieved, resulting in a hair that has the desired shape and looks natural because the hair does not have a heavy coating on it."

In particular, it is preferred that the volatile styling active is selected from the group consisting of hydrophobic style achievement agent, water, and mixtures thereof.

Moreover, it is preferred that the hydrophobic style achievement agent is selected from the group consisting of volatile silicones, branched chain hydrocarbons, alkoxy-fluoroalkanes, low viscosity alkyl methicone fluids and mixtures thereof.

Furthermore, it is preferred that the volatile silicone is selected from the group consisting of decamethyl cyclopentasiloxane, hexamethyldisiloxane, cyclotetradimethylsiloxane and mixtures thereof. It is also preferred that the alkoxy-fluoroalkanes is methoxy-fluorobutane.

It is preferred that the low viscosity alkyl methicone fluid is selected from the group consisting of hexylmethicone, caprylil methicone and mixtures thereof. It is also preferred that the volatile styling active is water.

Further features of the present invention and advantages brought thereby will be understood in detail from the following descriptions of the preferred embodiment of the present invention referring to the attached drawings.

BRIEF EXPLANATION OF THE DRAWINGS

FIGS. 6A and 6B are perspective views of an unfitted state, and a fitted state of a supplementary liquid injection unit and the liquid storage container.

FIGS. 7A and 7B are cross-sectional views of the unfitted state, and the fitted state of the principal portion of the supplementary liquid injection unit and the liquid storage container.

In FIGS. 8A and 8B.

FIGS. 11A and 11B are side and front views showing the state of use of the hair iron.

In FIGS. 12A and 12B, FIG. 12A is a plan view of the holding surface, and FIG. 12B is an enlarged view of an area D of FIG. 12A according to another embodiment of the present invention.

FIG. 13 is a front cross-sectional view of a holding part of the hair iron.

BEST MODE FOR CARRYING OUT THE INVENTION

Figure 1:
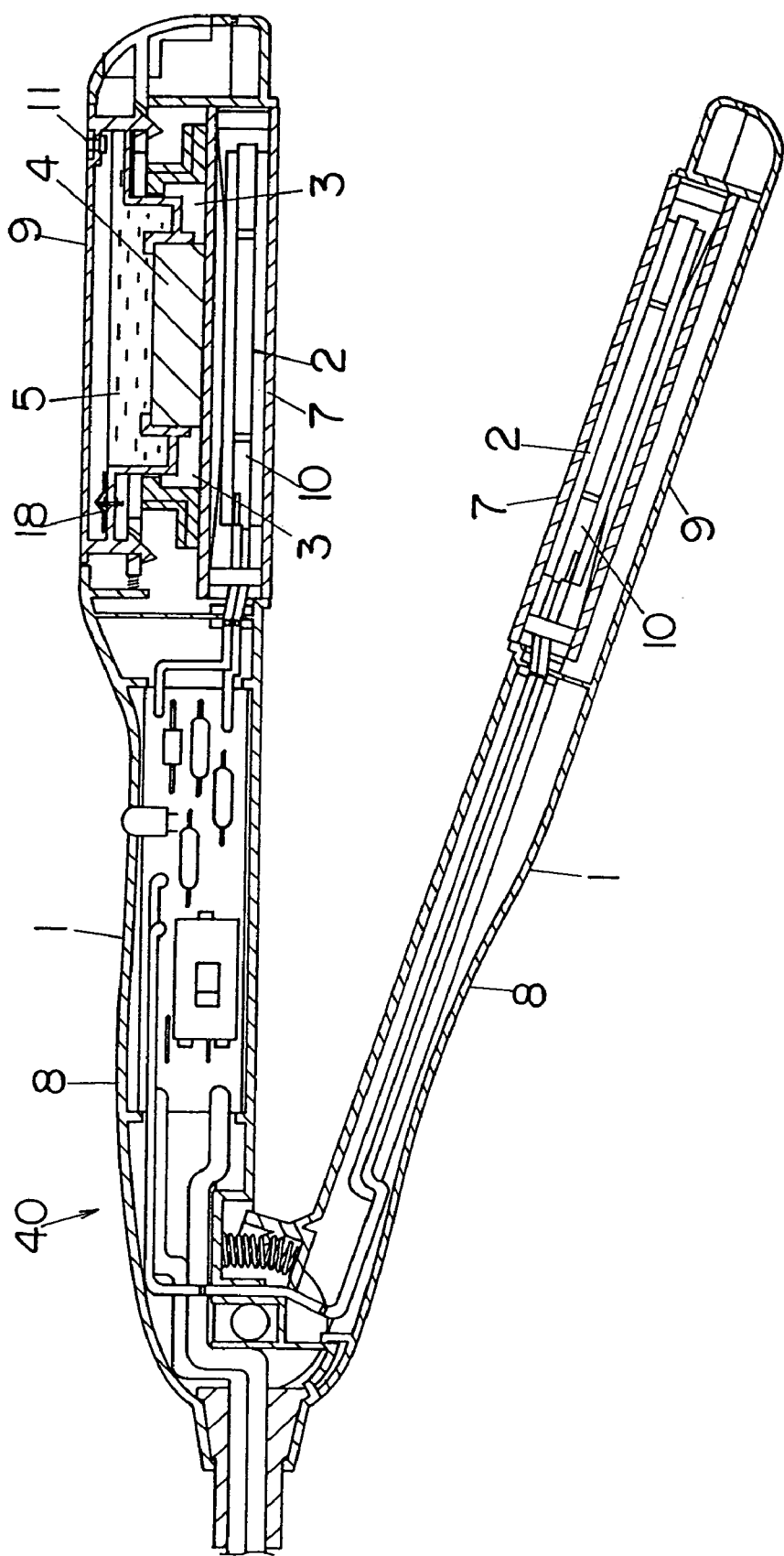
FIG. 1 is a side cross-sectional view of a hair iron according to a preferred embodiment of the present invention.
Figure 2:
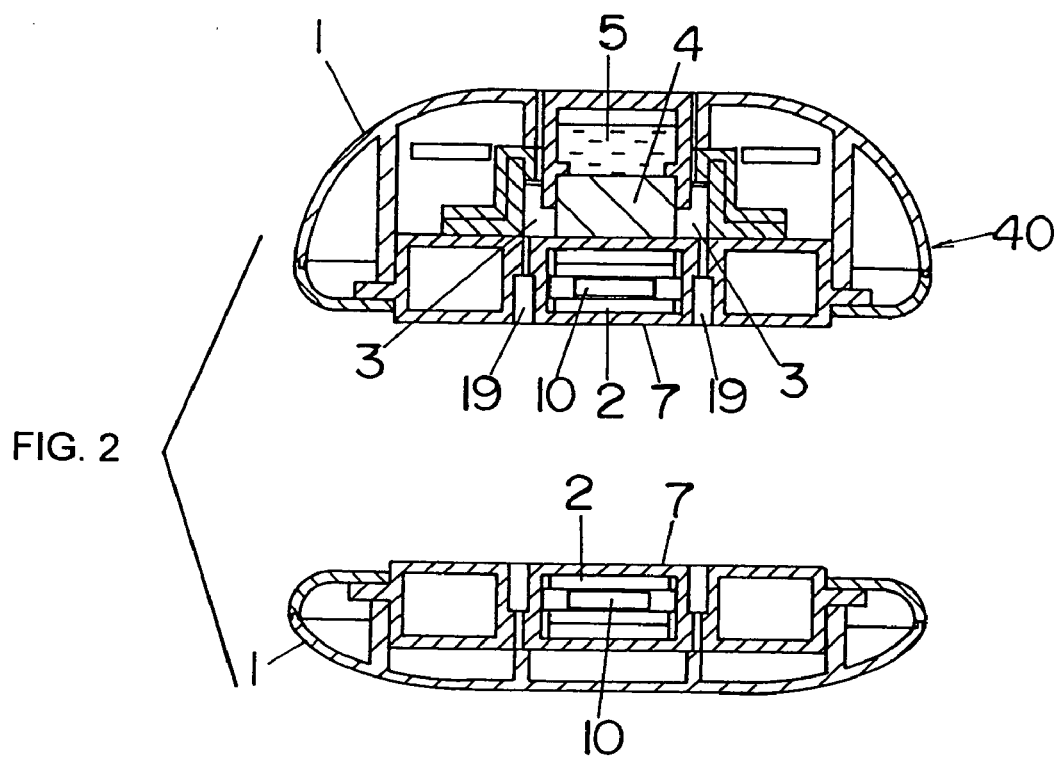
FIG. 2 is a front cross-sectional view of the hair iron.

In the following, embodiments of the present invention will be explained with reference to figures. In an embodiment of the present invention, as shown in FIGS. 1 and 2, a hair iron (40) has its main body composed of a pair of holding parts (1, 1) which are in elongated shape and have their ends on one side in the longitudinal direction hinged together to form a V-shape that can be opened/closed at will.

For two holding parts (1, 1), handle portions (8, 8) are formed on their ends on one side that are hinged, while holding portions (9, 9) are formed on the ends on the other side. The holding portion (9) contains a heating block (2) made of a heater (10) composed of a PTC element. The surface of the heating block (2) is exposed on the opposing surface of holding part (1), and it becomes a holding surface (7) with an elongated planar shape. Since the main body is V-shaped, it is possible to adjust the force for holding the hair between holding surfaces (7, 7) easily, and, by means of the PTC element in the heater (10), the temperature can be automatically controlled.

Figure 3A:
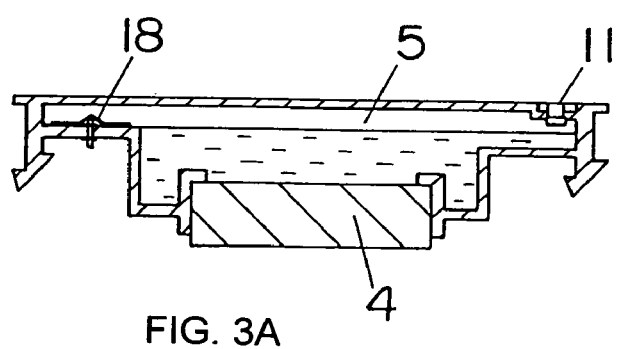
FIGS. 3A and 3B are side and front cross-sectional views of a liquid holder and a liquid container formed integrated to each other of the hair iron.
Figure 3B:
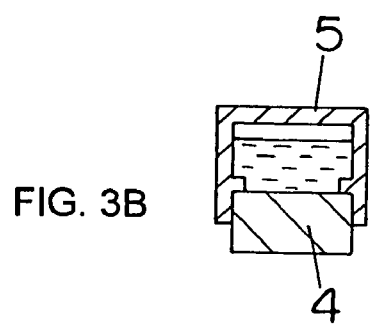

In one of the two holding parts (1, 1), as shown in FIGS. 3A and 3B, a liquid container (5) is formed as a hollow structure for storing liquid, and a liquid holder (4) is in the form of a flat, porous element with almost uniform thickness. The liquid holder (4) and the liquid container (5) are formed so that they are installed as a single unit in a quick-connecting-disconnecting manner with respect to the holding part (1). When they are installed, the surface of the liquid holder (4) on the opposite side connected to the liquid container (5) is in contact with the heating block (2), and the liquid container (5) and the heating block (2) are connected to each other via the liquid holder (4). Consequently, the liquid in the liquid holder (4) moves a prescribed distance in the thickness direction inside the liquid container (5) that has a nearly uniform thickness, and it moves to the contact surface with the heating block (2), where it evaporates.

In this way, the liquid container (5) is set on the side of the heating block (2) opposite to the holding surface (7), and, at the same time, the liquid holder (4) is set between the heating block (2) and the liquid container (5). In this way, the liquid in the liquid container (5) is transferred uniformly inside the liquid holder (4) until it reaches the contact surface with the heating block (2), and the liquid evaporates steadily, with good efficiency over the entire contact surface of the liquid holder (4) by means of the heating block (2).

Figure 4A:
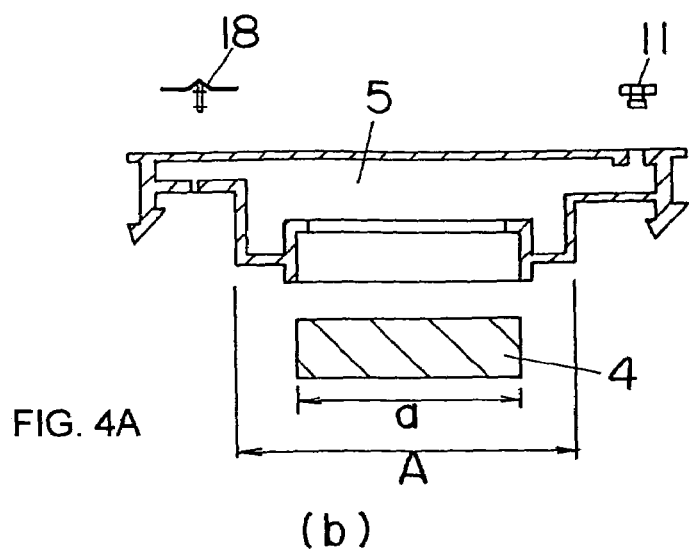
FIGS. 4A and 4B are side and front cross-sectional views of the liquid holder and the liquid container in disassembled state.
Figure 4B:
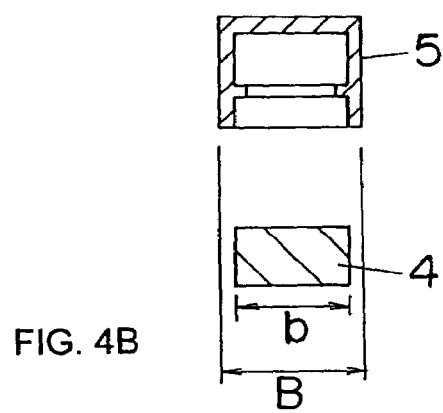

The contact surface of the liquid holder (4) with the heating block (2) has an elongated shape in agreement with the longitudinal direction of the holding surface (7). As shown in FIGS. 4A and 4B, if the length of the contact surface is "a", its width "b", and the main body of the liquid container (5) has a length "A" and a width "B", "a"<"A" and "b"<"B". In this way, the dimensions of the liquid container (5) in any direction are formed so as to be nearly equal to or greater than the dimensions of the liquid holder (4) in the same direction. As a result, it is possible to have a sufficient volume for the liquid container (5), so that evaporation can be continued for a long time.

Also, in this embodiment, one end of the liquid holder (4) in the thickness direction is only partially located and connected inside the liquid container (5), and even when the orientation of the holding part (1) itself is changed from a horizontal position (holding part (1) perpendicular to hair fiber) to a vertical position (holding part (1) parallel to hair fiber), the liquid inside the liquid container (5) can still make contact with the liquid holder (4) free of problem, and it is possible to continue evaporation.

Furthermore, since an amount of steam is determined by the contact surface area of the liquid holder (4) with the heating block (2), it is possible to finely adjust the steam volume by changing the contact surface area of the liquid holder (4).

When the liquid container (5) is installed, an inner pressure adjusting valve (18) and a cap-shaped supplementary liquid injection unit (11) are set, as shown in FIG. 3A. For the inner pressure adjusting valve (18), when the pressure inside liquid container (5) is lower than the ambient pressure by a prescribed pressure, the valve is opened, so that the difference between the inner pressure and outer pressure is released. As a result, the liquid is drawn into the liquid holder (4), so that it is possible to prevent the inner pressure of the liquid container (5) from decreasing too much to draw the liquid from the liquid container (5) with the liquid holder (4).

Also, as shown in FIGS. 6A, 6B, 7A and 7B, a main body portion (17) of the supplementary liquid injection unit (11) is a cylindrical element with a bottom equipped with a recessed connecting path (12). In the opening portion of the connecting path (12), fitting portion (16) is composed of a central annular portion (16a) and radial supporting elements (16b) that connect the annular portion (16a) and the inner peripheral surface of the connecting path (12). Also, a connecting hole (15), which connects the interior of the connecting path (12) and the interior of the liquid container (5), is formed through the side peripheral wall of the main body portion (17).

The interior of the main body portion (17) contains a circular-plate-shaped sealing plate (13) that seals the connecting path (12) and a spring (14) that is located between the sealing plate (13) and the inner bottom surface of the connecting path (12) and energizes the sealing plate (13) towards the opening side of the connecting path (12). In the normal state, under the energizing force of the spring (14), the sealing plate (13) located at a prescribed distance from the inner bottom surface seals the connecting path (12) on the open side with respect to the connecting hole (15), and the interior of liquid container (5) is not opened via the connecting hole (15). Also, a cylindrical engaging portion (13a) is formed protruding from the center of the sealing plate (13), and, at the same time, the engaging portion (13a) is fitted to the annular portion (16a) in a freely sliding manner.

Figure 5:
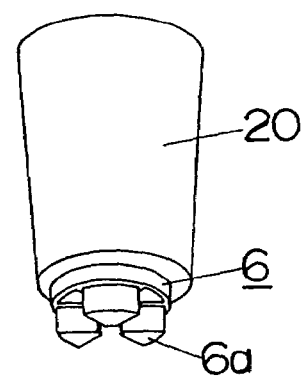
FIG. 5 is a perspective view of a liquid storage container.

As shown in FIG. 5, at an end of a liquid storage container (20) that is set as an element separated from the hair iron (40), a liquid supply unit (6) having protruding portions (6a), each of which can be inserted through a gap between adjacent supporting elements (16b, 16b) of the fitting portion (16), is set. As shown in FIGS. 7A and 7B, the protruding portion (6a) that is fitted with the fitting portion (16) and is inserted into the connecting path (12) pushes the sealing plate (13) towards the inner bottom surface side against the energizing force of the spring (14). In this case, at least part of the connecting hole (15) becomes located on the opening side with respect to the sealing plate (13), so that the interior of the liquid container (5) opens to the outside via the connecting hole (15) and the connecting path (12).

Similarly to a main body portion (17') of the supplementary liquid injection unit (11), the liquid supply unit (6) arranged in the liquid storage container (20) also has a similar spring (14') and a sealing plate (13'), and, there is also protruding portion (6a) formed from the main body portion (17'). When the protruding portion (6a) of the liquid supply unit (6) is fitted into the connecting path (12) via the fitting portion (16), as explained above, the sealing plate (13) of the supplementary liquid injection unit (11) is pushed on the protruding portion (6a), so that the interior of the liquid container (5) is opened, and, at almost the same time, engaging portion (13a') formed protruding from the sealing plate (13') of the liquid supply unit (6) engages with the engaging portion (13a) of the sealing plate (13), so that the sealing plate (13') is pushed in, and the interior of the liquid storage container (20) is opened via the connecting hole (15') of the main body portion (17'). That is, only when the protruding portion (6a) of the liquid supply unit (6) is fitted to the connecting path (12) of the supplementary liquid injection unit (11), the interior of the liquid container (5) is connected to the interior of the liquid storage container (20) via the supplementary liquid injection unit (11) and the liquid supply unit (6), and the liquid in the liquid container (5) is replenished from the liquid storage container (20).

Figure 8A:
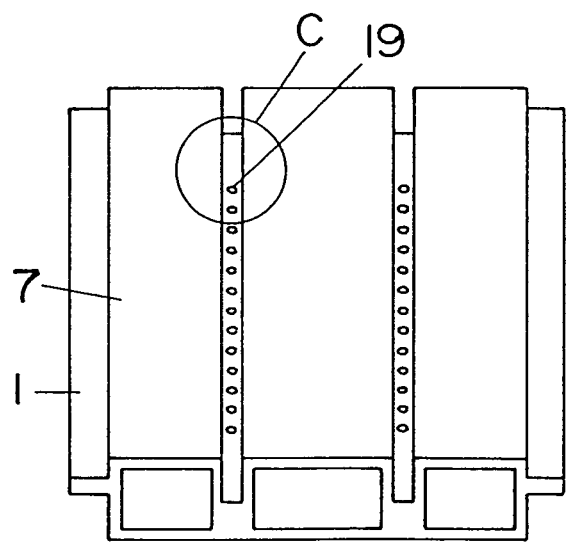
FIG. 8A is a plan view of a holding surface of the hair iron.
Figure 8B:
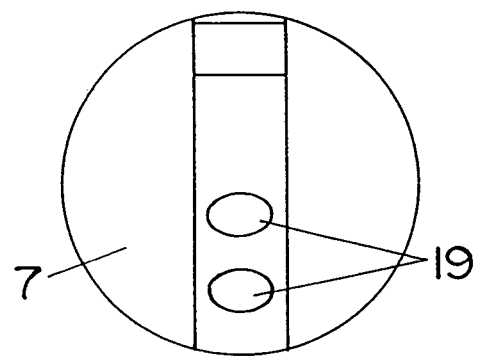
FIG. 8B is an enlarged view of an area C of FIG. 8A.

As shown in FIGS. 1 and 2, in the state in which the liquid holder (4) and the liquid container (5) are installed, steam chambers (3) defined by side surfaces of the liquid holder (4) and the back side of the heating block (2) are formed on the both sides of the liquid holder (4), respectively. In the heating block (2), multiple steam paths (19) are arranged at prescribed intervals in the longitudinal direction of the holding surface (7) through the heating block (2) from the steam chambers (3) on the two sides to holding surface (7). As shown in FIGS. 8A and 8B, the liquid that is transferred via the liquid holder (4) is heated, and the generated steam is filled uniformly in the longitudinal direction inside the steam chambers (3), and, at the same time, the steam is uniformly sprayed from the multiple steam paths (19) opened on the holding surface (7).

Figure 9:
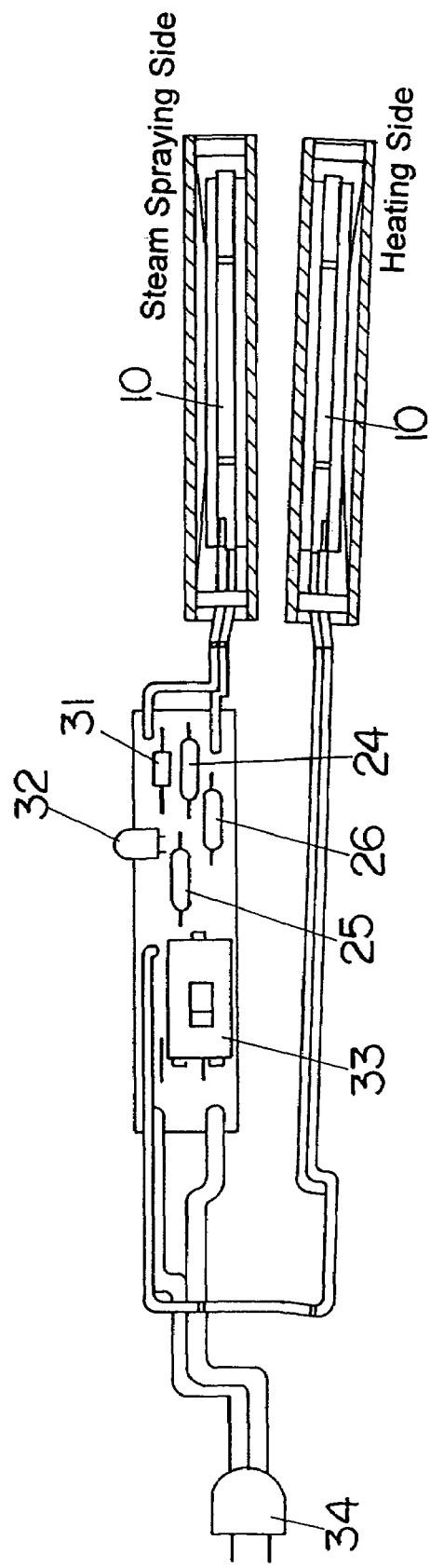
FIG. 9 is a diagram illustrating a circuit of the hair iron.
Figure 10:
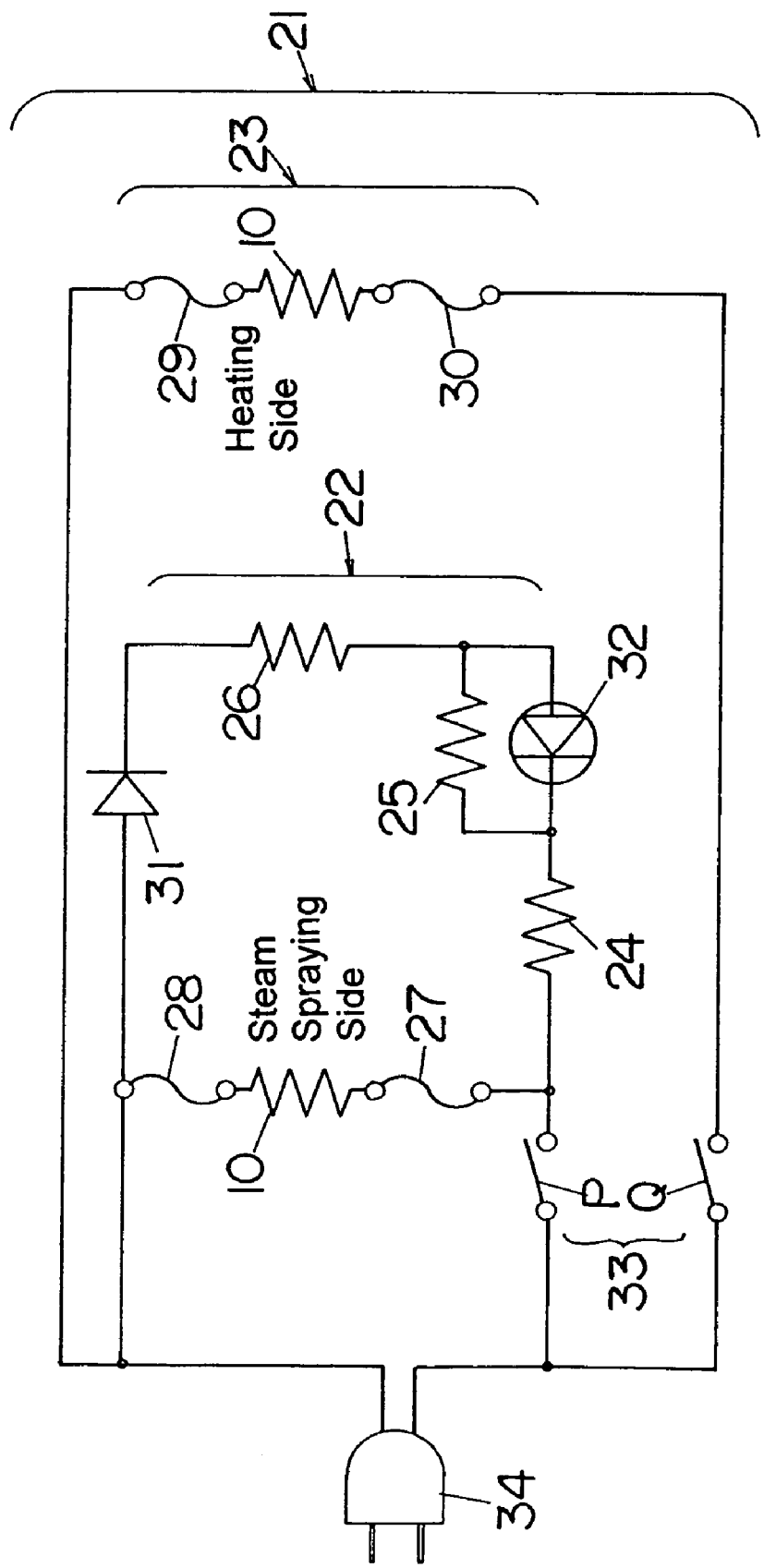
FIG. 10 is a circuit diagram of the hair iron.

In this embodiment, one of the holding parts (1, 1) of the hair iron (40) contains the liquid holder (4) and the liquid container (5) in addition to the heating block (2), so that it acts as the holding part (1) on the steam spraying side. The other holding part equipped with the heating block (2) acts as the holding part on the heating side. As shown in FIGS. 9 and 10, a circuit (21) for selectively supplying electric power to the heater (10) on the steam spraying side and the heater (10) on the heating side has a constitution in which a circuit (22) on the steam spraying side and a circuit (23) on the heating side, both of which have the heaters (10), are connected to a plug (34). Also, a power source switch unit (33) is composed of a steam switch P that turns on/off power to the heater (10) on the steam spraying side and a heating switch Q that turns on/off power to the heater (10) on the heating side. In FIG. 10, the numerals (24) to (26) represent resistors, (27) to (30) represent fuses, (31) represents a diode, and the numeral (32) represents a light-emitting diode.

The hair iron (40) with the aforementioned constitution is used as follows. The user fills the liquid container (5) with the liquid. Then, the steam switch P and the heating switch Q are turned on, and, as shown in FIGS. 11A and 11B, the hair is held between the holding surfaces (7, 7) of the holding parts (1, 1) facing each other. In this state, power is fed to the heaters (10, 10) of the heating blocks (2, 2) on the two sides, that is, the steam spraying side and heating side. While steam is fed from the heating block (2) on one side to the hair, the hair that has been wetted with steam is dried with the heating block (2) on the other side. In this way, the hairstyle can be set for the hair held between the holding surfaces (7, 7). In this case, the holding surfaces (7, 7) have an elongated planar shape with the longitudinal direction orthogonal to the hairstyle setting direction. The steam paths (19) are also set almost equidistantly in the direction orthogonal to the hairstyle setting direction, and steam is sprayed uniformly from the steam paths (19). Consequently, while the user has her/his hair held between the holding surfaces (1, 1), heat and steam are fed uniformly to all the hair, and, as the hair is pulled in the hairstyle direction, the hair can be set in a straight style with good efficiency.

When the steam switch P is turned on and the heating switch Q is turned off, power is fed only to the heater (10) of the heating block (2) on the steam spraying side, so that only steam is applied to the hair. On the other hand, when the steam switch P is turned off, while the heating switch Q is turned on, power is fed only to the heater (10) of the heating block (2) on the heating side, so that the hair iron only acts to dry the hair in this mode.

When the liquid is to be replenished, the liquid holder (4) and the liquid container (5) are removed together as a single unit, and replenishment is performed by means of the dedicated liquid storage container (20). In this case, since the holding part (1) is removed temporarily to enable replenishment, the liquid can easily be injected. At the same time, it is possible to prevent the hair iron (40) itself from becoming contaminated with the liquid, and it is possible to prevent short-circuits of the electrical circuit and internal damage due to invasion of the liquid into the hair iron. Because only when the supplementary liquid injection unit (11) is fitted to the liquid storage container (20) the liquid can be replenished, it is possible to prevent replenishment of the liquid from the wrong container or means. As a result, it is possible to prevent inadvertent mistakes in injecting and using undesired liquids.

In this embodiment, the hair iron (40) can dispense a treatment agent comprised of water. In yet another embodiment, the hair iron (40) can dispense a 50/50 blend of cyclopentadimethylsiloxane and hexamethyldisiloxane.

The present invention provides a treatment agent to the hair in order to achieve a desired style. The treatment agent can provide a style achievement by providing conditioning/lubrication benefit to hair fibers and/or making it easier to reshape hair. All of this results in a hair that is more manageable and can more easily take the new desired shape.

The treatment agent of the present invention may be any known or otherwise effective volatile liquid that ease hair manageability and will evaporate from hair, while or after shape has been achieved, resulting in a hair that has the desired shape and looks natural because the hair does not have a heavy coating on it.

Suitable styling achievement actives for use in the present invention are volatile components that will not remain on hair. In this context, the term "volatile" refers to materials which have a boiling point of less than about 260° C., preferably from about 50° C. to about 260° C., more preferably from about 60° C. to about 150° C. (at about one atmosphere of pressure).

Nonlimiting examples of volatile style achievement agents include water; organic solvents such as $C_1$-$C_6$ alkanols and combinations thereof. Specific examples of suitable $C_1$-$C_6$ alkanols include, but are not limited to, ethanol, n-propanol, isopropanol, n-butanol, amyl alcohol, and mixtures thereof. Preferred $C_1$-$C_6$ alkanols include $C_2$-$C_4$ monohydric alcohols such as ethanol, isopropanol, and mixtures thereof. Water is the preferred volatile styling active.

Hydrophobic style achievement agents will provide a conditioning/lubrication benefit during the styling process to make hair more manageable, are represented, but are not limited to volatile silicones, branched chain hydrocarbons, alkoxy-fluoroalkanes and mixtures thereof. Hydrophobic branched chain hydrocarbons useful as a hydrophobic style achievement agent herein include, but are not limited to, those containing from about 7 to about 14, more preferably from about 10 to about 13, and most preferably from about 11 to about 12 carbon atoms. Saturated hydrocarbons are preferred, although it is not intended to exclude unsaturated hydrocarbons. Examples of such preferred branched chain hydrocarbons include isoparaffins of the above chain sizes.

Specific examples of isoparaffins include Isopar E ($C_8$-$C_9$ isoparaffins), Isopar H and K ($C_{11}$-$C_{12}$ isoparaffins), and Isopar L ($C_{11}$-$C_{13}$ isoparaffins) or mixtures thereof (all commercially available form Exxon Chemical Co.) Other suitable branched chain hydrocarbons are isododecane and isoundecane. Isododecane is preferred and is commercially available from Presperse, Inc. as Permethyl TM 99A.

Preferred silicones useful as a hydrophobic style achievement agent include, but are not limited to, volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cylcopentasiloxane, and mixtures thereof. More preferred among the volatile silicones are hexamethyl disiloxane and cyclomethicones, examples of which include octamethyl cyclo tetrasiloxane and decamethyl cyclopentasiloxane, which are commonly referred to as D4 and D5 cyclomethicone, respectively.

Additional examples of preferred volatile silicones, include, but are not limited to, cyclopentasiloxane (commercially available from General Electric Co. as SF1202), hexylmethicone (commercially available from Archimica as Silcare 41M10), caprylil methicone (commercially available from Archimica as Silcare 41M15), stearoxytrimethylsilane and mixtures thereof. The volatile silicones are preferably cyclopentadimethylsiloxane and hexamethyldisiloxane. Hydrophobic style achievement agents can include alkoxyfluoroalkane volatile fluids, examples of which include methoxy-fluorobutane (Fluid HFE-7100 by Archimica Nove).

The styling achievement agent of the present invention may be delivered by from about 0.01 to about 2 gram/minute/side of the hair iron, preferably from about 0.1 to about 1 gram/minute/side, and preferably from about 0.15 to about 0.4 gram/minute/side.

The styling achievement agent of the present invention may include any of the following materials mentioned and described in below, either alone or in combination.

In addition to the treatment agents described above, the present invention may further comprise one or more optional components known or otherwise effective for use in hair care or personal care products, provided that the optional components are physically and chemically compatible with the components described above, or do not otherwise unduly impair product stability, aesthetics or performance. Nonlimiting examples of such optional components are disclosed in *International Cosmetic Ingredient Dictionary*, Fifth Edition, 1993, and *CTFA Cosmetic Ingredient Handbook*, Second Edition, 1992, both of which are incorporated by reference herein in their entirety.

The compositions of the invention can contain adjuvants that are common in the cosmetics field, such as sunscreens; anti-free-radical agents; antioxidants; preserving agents; acidifying or basifying agents; fragrances; dyestuffs; reducing agents. The amounts of these various adjuvants are those used conventionally in the fields considered.

The present invention may, in some embodiments, further comprise additional optional components known or otherwise effective for use in hair care or personal care products. The concentration of such optional ingredients generally ranges from zero to about 25%, more typically from about 0.05% to about 25%, even more typically from about 0.1% to about 15%, by weight of the composition. Such optional components should also be physically and chemically compatible with the essential components described herein, and should not otherwise unduly impair product stability, aesthetics or performance.

The compositions of the present invention may be prepared by any known or otherwise effective technique, suitable for providing a composition provided that the resulting composition provides the excellent style achievement benefits described herein. Methods for preparing the embodiments of the present invention include conventional formulation and mixing techniques.

In the following, a hair iron (40) will be explained as another embodiment of the present invention. The basic constitution is the same as the aforementioned embodiment and its description will not be repeated. The characteristic features of this embodiment will now be explained. As shown in FIGS. 12A, 12B and 13, a holding surface (7) formed on a holding part (1) has a curved surface that is wavy in the direction orthogonal to the longitudinal direction, i.e., in the hairstyle setting direction. Since the holding parts (1, 1) are closed, the holding surfaces (7, 7) match each other. Consequently, while hair is held between the holding surfaces (7, 7), it is possible to apply heat and steam uniformly to all the hair, so that it is possible to set a wavy hairstyle with good efficiency.

Figure 14:
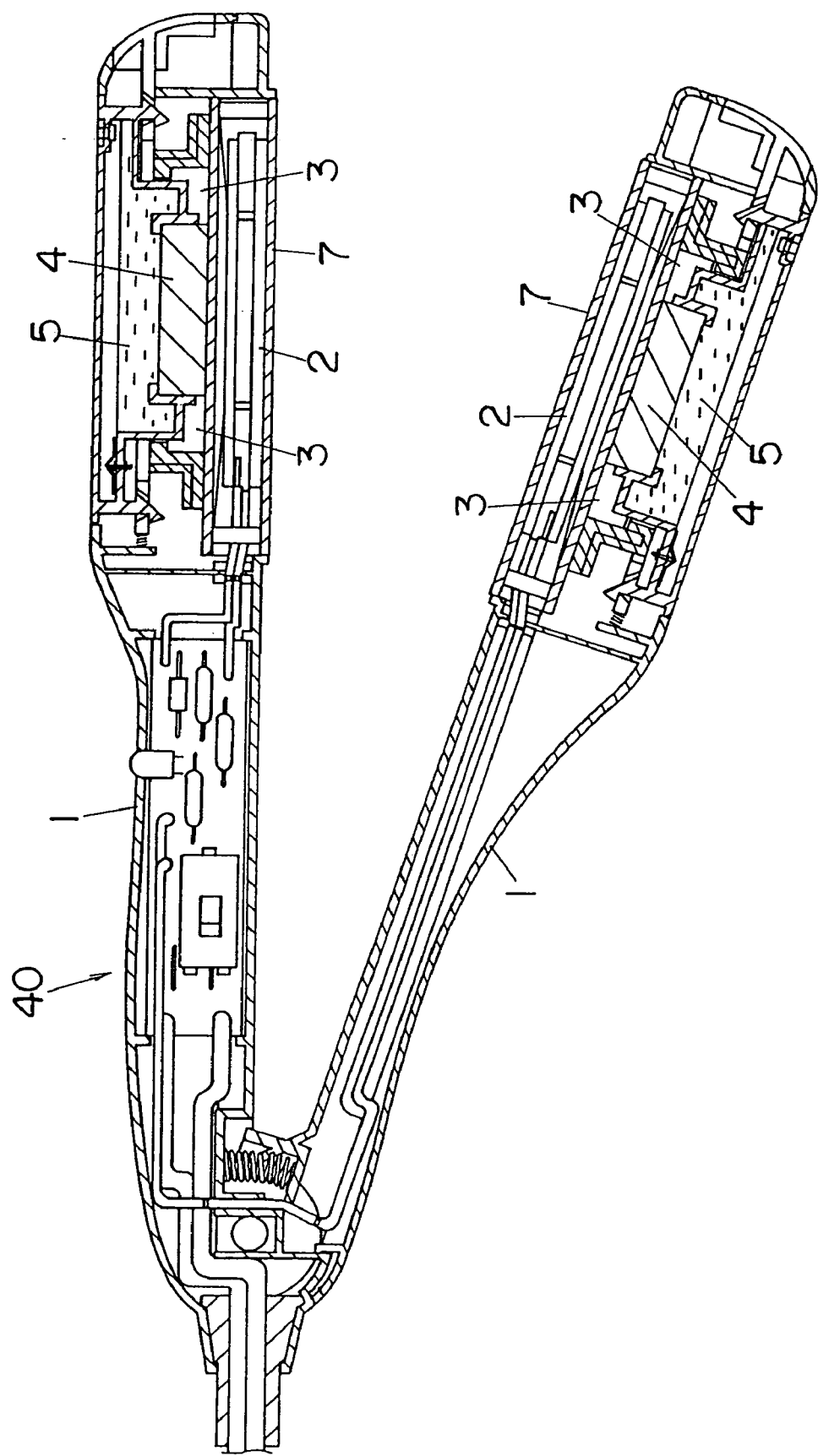
FIG. 14 is a side cross-sectional view of the hair iron according to yet another embodiment of the present invention.
Figure 15:
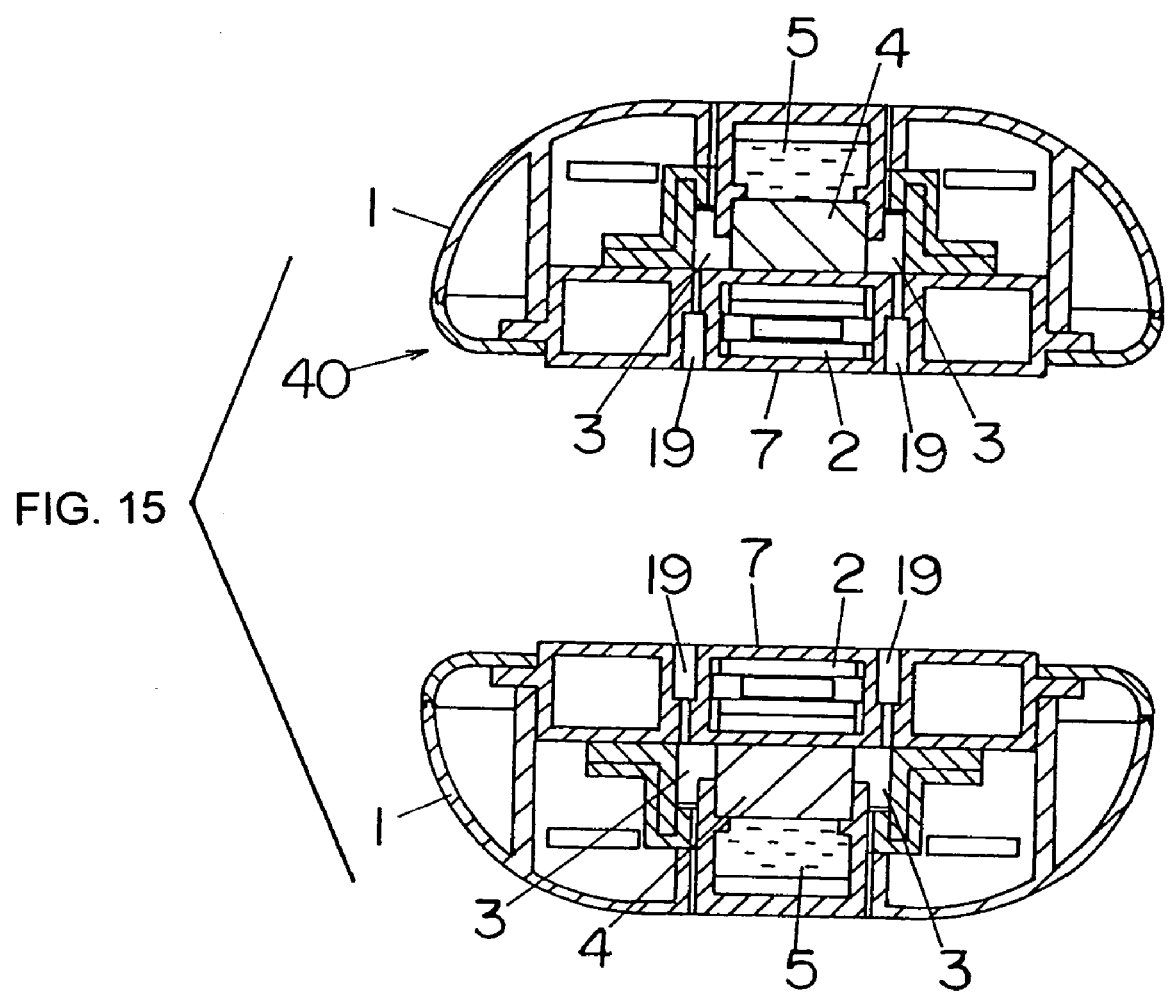
FIG. 15 is a front cross-sectional view of the hair iron of FIG. 14.

In the following, a hair iron (40) in yet another embodiment of the present invention will be explained. The basic constitution is the same as that of the aforementioned embodiment and its description will not be repeated. The characteristic features of this embodiment will be explained. As shown in FIGS. 14 and 15, each of a pair of holding parts (1, 1) has the liquid holder (4), liquid container (5) and the steam paths (19) in addition to the heating block (2). Consequently, steam is sprayed from both holding surfaces (7, 7) onto the two sides that hold the hair. In this way, it is possible effectively to apply steam to penetrate the hair.

By the way, when a holding part (1) is arranged only on one side with respect to the liquid container (5), and the liquid is transferred from the holding parts (1, 1) on the two sides to the heating blocks (2, 2), it is necessary to transfer the liquid from the liquid container (5) of the holding part (1) on one side to the heating block (2) of the holding part (1) on the other side. Compared with this method, in the aforementioned constitution in which the liquid containers (5) are set on two sides, respectively, it becomes easier to transfer the liquid.

As a modification of the hair iron (40) of the present invention, the holding surface (7) may also have a wavy surface with waves in the direction perpendicular to the longitudinal direction.

INDUSTRIAL APPLICABILITY

As described above, according to the hair iron of the present invention, since steam of the liquid is uniformly provided to the outside from the holding surface of the hair iron, the user can efficiently set a desired hairstyle. In addition, since the structure of the hair iron of the present invention presents an increased generation amount of steam, it is possible to effectively give a desired treatment effect to the hair to be set. Thus, by using the hair iron of the present invention, the use can easily and efficiently achieve the desired hairstyling. Therefore, this invention meets the requirements of being industrially applicable.

BRIEF DESCRIPTION OF PART NUMBERS

1 Holding part
2 Heating block
3 Steam chamber
4 Liquid holder
5 Liquid container
6 Liquid supply unit
7 Holding surface
8 Handle
11 Supplementary liquid injection unit
12 Connecting path
13 Sealing plate
14 Spring
15 Connecting hole
19 Steam path
20 Liquid storage container
33 Power source switch unit
40 Hair iron
41 Liquid absorber

The invention claimed is:

1. A hair iron characterized in that it comprises a pair of holding parts, where each holding part has at least one heating block with its surface formed as a holding surface; at least one of said holding parts in turn comprising a liquid container, a liquid holder that brings the liquid in the liquid container in contact with the heating block as the liquid in the liquid container is transferred to the heating block, and a steam path that sprays from the holding surface the steam generated as the liquid transferred from inside the liquid container is heated by the contact surface of the heating block with the liquid holder; wherein hair is held between the holding surfaces of said pair of holding parts, and, under the action of the steam sprayed from the steam path, the hairstyle is set; and wherein the liquid container is set on the side of the heating block opposite the holding surface, and, at the same time, the liquid holder is arranged between the heating block and the liquid containers, wherein a supplementary liquid injection unit is arranged in the liquid container, and, at the same time, a connecting means is arranged such that it can supply liquid from a liquid storage container arranged as a separate part only when a liquid supply unit of said liquid storage container is fitted to said supplementary liquid injection unit, and wherein as said connecting means, the supplementary liquid injection unit is equipped with a recessed connecting path in which the liquid supply unit of the liquid storage container can be inserted and fitted, a sealing plate that seals the connecting path, and a spring that energizes the sealing plate in the direction towards the opening of the connecting path; in the state in which the liquid supply unit is not fitted, the connecting hole that connects the interior of the connecting path and the interior of the liquid container is located on the side of the inner bottom surface of the connecting path with respect to the sealing plate that is energized and positioned by the spring in the direction towards the opening of the connecting path; and in the state in which the liquid, supply unit is fitted, at least part of the connecting hole is located on the side of the opening of the connecting path with respect to the sealing plate that is pressed and positioned in said liquid supply unit.

2. The hair iron as set forth in claim 1, wherein with respect to each dimension of the various directions of the contact surface of the liquid holder with the heating block, the dimension of the liquid container in the same direction is formed nearly the same or larger.

3. The hair iron as set forth in claim 1, wherein part of the liquid holder is located inside the liquid container.

4. The hair iron as set forth in claim 1, wherein the liquid container and liquid holder are integrally formed.

5. The hair iron as set forth in claim 4, wherein the liquid container and liquid holder are arranged such that they allow quick-connecting-disconnecting as a single unit with/from the holding part.

6. The hair iron as set forth in claim 1, wherein the contact surface of the liquid holder with the heating block has an elongated form extending in the longitudinal direction of the holding surface, and at the same time, a steam chamber is formed on the side of the liquid holder; multiple steam paths that go from said steam chamber through to the holding surface are formed at prescribed longitudinal intervals.

7. The hair iron as set forth in claim 6, wherein steam chambers are formed on both sides of the liquid holder, and steam paths are formed for connecting from said steam chambers.

8. The hair iron as set forth in claim 1, wherein said holding parts have an elongated form, with a holding surface formed on one end and a handle on the other end, and wherein the aforementioned handle ends of said holding parts are connected together so that one of said holding parts can be pivotally moved relative to the other one of said holding parts about the aforementioned handle ends.

9. The hair iron as set forth in claims 1, wherein one of said holding parts is a holding part on a steam spraying side, which is equipped with the liquid container, the heating block, the liquid holder, and the steam path, and the other holding part is a holding part on a heating side; and wherein said hair iron has a power source switch unit for switching between a first power supply mode where either electric power is supplied to the heating blocks of both holding parts and a second power supply mode where electric power is supplied only to the heating block of the holding part on the steam spraying side or the heating side.

10. The hair iron as set forth in claim 1, wherein both of said pair of holding parts are equipped with heating block, liquid holder, and steam path.

11. The hair iron as set forth in claim 1, wherein the liquid injected into the liquid container is a treatment agent.

12. The hair iron as set forth in claim 11, wherein the treatment is a volatile styling active and mixtures thereof.

13. The hair iron as set forth in claim 12, wherein the volatile styling actives is selected from the group consisting of hydrophobic style achievement agent, water, and mixtures thereof.

14. The hair iron as set forth in claim 13, wherein the hydrophobic style achievement agent is selected from the group consisting of volatile silicones, branched chain hydrocarbons, alkoxy-fluoroalkanes, low viscosity alkyl methicone fluids and mixtures thereof.

15. The hair iron as set forth in claim 14, wherein the volatile silicone is selected from the group consisting of decamethyl cyclopentasiloxane, hexamethyldisiloxane, cyclotetradimethylsiloxane and mixtures thereof.

16. The hair iron as set forth in claim 14, wherein the alkoxy-fluoroalkanes is methoxy-fluorobutane.

17. The hair iron as set forth in claim 14, wherein the low viscosity alkyl methicone fluid is selected from the group consisting of hexylmethicone, caprylil methicone and mixtures thereof.

18. The hair iron set forth in claim 13, wherein the volatile styling active is water.

* * * * *